US012414766B2

(12) United States Patent
Amariglio et al.

(10) Patent No.: US 12,414,766 B2
(45) Date of Patent: Sep. 16, 2025

(54) SURGICAL HANDLE ASSEMBLY

(71) Applicant: Lexington Medical, Inc., Billerica, MA (US)

(72) Inventors: Leon Amariglio, Lexington, MA (US); Gonen Somekh, Kerem Maharal (IL); Shani Mann, Needham, MA (US)

(73) Assignee: Lexington Medical, Inc., Bedford, MA (US)

( * ) Notice: Subject to any disclaimer, the term of this patent is extended or adjusted under 35 U.S.C. 154(b) by 804 days.

(21) Appl. No.: 17/382,705

(22) Filed: Jul. 22, 2021

(65) Prior Publication Data
US 2021/0346021 A1    Nov. 11, 2021

Related U.S. Application Data

(63) Continuation of application No. 16/582,829, filed on Sep. 25, 2019, now Pat. No. 11,103,247, which is a
(Continued)

(51) Int. Cl.
*A61B 17/072* (2006.01)
*A61B 17/00* (2006.01)
(Continued)

(52) U.S. Cl.
CPC ...... *A61B 17/07207* (2013.01); *A61B 17/072* (2013.01); *A61B 2017/0023* (2013.01);
(Continued)

(58) Field of Classification Search
CPC ................ A61B 17/068; A61B 17/072; A61B 17/07207; A61B 17/115; A61B 17/29; A61B 17/2909; A61B 2017/00473; A61B 2017/00477; A61B 2017/07214; A61B 2017/07271; A61B 2017/2927; A61B 2017/2923; A61B 2017/2943
(Continued)

(56) References Cited

U.S. PATENT DOCUMENTS

RE28,932 E    8/1976  Noiles et al.
4,403,722 A   9/1983  Nikolich
(Continued)

FOREIGN PATENT DOCUMENTS

CN    101507643 A    8/2009
CN    101664331 A    3/2010
(Continued)

OTHER PUBLICATIONS

European Search Report and Opinion for related EP Application No. 18781498.3, dated Mar. 29, 2022, 6 pages.
(Continued)

*Primary Examiner* — Scott A Smith
(74) *Attorney, Agent, or Firm* — Perkins Coie LLP

(57) ABSTRACT

The present disclosure includes apparatuses for a surgical handle assembly. An example apparatus includes a movable handle member and a switch configured to provide two or more modes of operation for the movable handle member and a driving pawl pivotally connected to a swing wheel configured to advance an actuation shaft linearly in a distal direction in response to actuation of the movable handle member.

20 Claims, 7 Drawing Sheets

Related U.S. Application Data continuation of application No. 15/481,949, filed on Apr. 7, 2017, now Pat. No. 10,433,842.

(51) Int. Cl.
  *A61B 17/068* (2006.01)
  *A61B 17/29* (2006.01)

(52) U.S. Cl.
  CPC .......... *A61B 2017/00367* (2013.01); *A61B 2017/00407* (2013.01); *A61B 2017/00464* (2013.01); *A61B 2017/00473* (2013.01); *A61B 17/068* (2013.01); *A61B 2017/07214* (2013.01); *A61B 2017/07257* (2013.01); *A61B 2017/07271* (2013.01); *A61B 2017/2923* (2013.01)

(58) Field of Classification Search
  USPC ....... 227/19, 175.2, 176.1, 180.1; 606/1, 75, 606/139, 213, 219
  See application file for complete search history.

(56) References Cited

U.S. PATENT DOCUMENTS

| | | | |
|---|---|---|---|
| 4,572,419 | A | 2/1986 | Klaus et al. |
| 4,725,764 | A | 2/1988 | Prestel |
| 4,737,608 | A | 4/1988 | Jones |
| 4,938,408 | A | 7/1990 | Bedi et al. |
| 4,978,049 | A | 12/1990 | Green |
| 5,199,419 | A | 4/1993 | Remiszewski et al. |
| 5,300,081 | A | 4/1994 | Young et al. |
| 5,326,013 | A | 7/1994 | Green et al. |
| RE34,680 | E | 8/1994 | Lieser |
| 5,467,911 | A | 11/1995 | Tsuruta et al. |
| 5,474,223 | A | 12/1995 | Viola et al. |
| 5,484,095 | A | 1/1996 | Green et al. |
| 5,489,058 | A | 2/1996 | Plyley et al. |
| 5,489,292 | A * | 2/1996 | Tovey ............... A61B 17/282 606/174 |
| 5,507,426 | A | 4/1996 | Young et al. |
| 5,522,534 | A | 6/1996 | Viola et al. |
| 5,535,935 | A | 7/1996 | Vidal et al. |
| 5,586,711 | A | 12/1996 | Plyley et al. |
| 5,588,579 | A | 12/1996 | Schnut et al. |
| 5,601,224 | A | 2/1997 | Bishop et al. |
| 5,736,703 | A | 4/1998 | Kim |
| 5,758,814 | A | 6/1998 | Gallagher et al. |
| 5,762,256 | A | 6/1998 | Mastri et al. |
| 5,799,857 | A | 9/1998 | Robertson et al. |
| 5,823,066 | A | 10/1998 | Huitema et al. |
| 5,836,503 | A | 11/1998 | Ehrenfels et al. |
| 5,865,361 | A | 2/1999 | Milliman et al. |
| 5,901,895 | A | 5/1999 | Heaton et al. |
| 6,109,500 | A | 8/2000 | Alli et al. |
| 6,281,453 | B1 | 8/2001 | Uleski |
| 6,302,798 | B1 | 10/2001 | Nakaguro et al. |
| 6,905,057 | B2 | 6/2005 | Swayze et al. |
| 6,945,444 | B2 | 9/2005 | Gresham et al. |
| 6,957,758 | B2 | 10/2005 | Aranyi |
| 7,044,352 | B2 | 5/2006 | Shelton et al. |
| 7,044,353 | B2 | 5/2006 | Mastri et al. |
| 7,083,075 | B2 | 8/2006 | Swayze et al. |
| 7,097,089 | B2 | 8/2006 | Marczyk |
| 7,128,254 | B2 | 10/2006 | Shelton et al. |
| 7,143,923 | B2 | 12/2006 | Shelton et al. |
| 7,143,924 | B2 | 12/2006 | Scirica et al. |
| 7,168,604 | B2 | 1/2007 | Milliman et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,246,734 | B2 | 7/2007 | Shelton |
| 7,303,106 | B2 | 12/2007 | Milliman et al. |
| 7,325,713 | B2 | 2/2008 | Aranyi |
| 7,364,060 | B2 | 4/2008 | Milliman |
| 7,380,695 | B2 | 6/2008 | Doll et al. |
| 7,380,696 | B2 | 6/2008 | Shelton et al. |
| 7,398,907 | B2 | 7/2008 | Racenet et al. |
| 7,404,508 | B2 | 7/2008 | Smith et al. |
| 7,416,101 | B2 * | 8/2008 | Shelton, IV ...... A61B 17/07207 227/176.1 |
| RE40,514 | E | 9/2008 | Mastri et al. |
| 7,422,136 | B1 | 9/2008 | Marczyk |
| 7,455,208 | B2 | 11/2008 | Wales et al. |
| 7,490,749 | B2 | 2/2009 | Schall et al. |
| 7,494,038 | B2 | 2/2009 | Milliman |
| 7,516,877 | B2 | 4/2009 | Aranyi |
| 7,546,940 | B2 | 6/2009 | Milliman et al. |
| 7,611,038 | B2 | 11/2009 | Racenet et al. |
| 7,624,902 | B2 | 12/2009 | Marczyk et al. |
| 7,658,311 | B2 | 2/2010 | Boudreaux |
| 7,694,865 | B2 | 4/2010 | Scirica |
| 7,753,245 | B2 | 7/2010 | Boudreaux et al. |
| 7,780,055 | B2 | 8/2010 | Scirica et al. |
| 7,784,663 | B2 | 8/2010 | Shelton |
| 7,794,475 | B2 | 9/2010 | Hess et al. |
| 7,802,712 | B2 | 9/2010 | Milliman et al. |
| 7,819,296 | B2 * | 10/2010 | Hueil ............... A61B 17/07207 227/19 |
| 7,824,426 | B2 | 11/2010 | Racenet et al. |
| 7,832,408 | B2 | 11/2010 | Shelton et al. |
| 7,837,079 | B2 | 11/2010 | Holsten et al. |
| 7,845,535 | B2 | 12/2010 | Scircia |
| 7,857,187 | B2 | 12/2010 | Milliman |
| 7,922,063 | B2 | 4/2011 | Racenet et al. |
| 7,926,692 | B2 | 4/2011 | Racenet et al. |
| 7,963,431 | B2 | 6/2011 | Scirica |
| 7,967,178 | B2 | 6/2011 | Scirica et al. |
| 7,967,180 | B2 | 6/2011 | Scirica |
| 8,020,743 | B2 | 9/2011 | Shelton |
| 8,056,789 | B1 | 11/2011 | White et al. |
| 8,061,576 | B2 | 11/2011 | Cappola |
| 8,070,036 | B1 * | 12/2011 | Knodel ............ A61B 17/07207 227/175.1 |
| 8,070,836 | B2 | 12/2011 | Ng et al. |
| 8,123,101 | B2 | 2/2012 | Racenet et al. |
| 8,136,712 | B2 | 3/2012 | Zingman |
| 8,141,763 | B2 | 3/2012 | Milliman |
| 8,157,148 | B2 | 4/2012 | Scirica |
| 8,186,555 | B2 | 5/2012 | Shelton et al. |
| 8,210,411 | B2 * | 7/2012 | Yates ................ A61B 17/3205 227/19 |
| 8,235,274 | B2 | 8/2012 | Cappola |
| 8,292,157 | B2 | 10/2012 | Smith et al. |
| 8,308,040 | B2 * | 11/2012 | Huang ................ A61B 17/068 227/181.1 |
| 8,328,822 | B2 * | 12/2012 | Huitema ............. A61B 17/10 606/142 |
| 8,336,751 | B2 | 12/2012 | Scirica |
| 8,336,754 | B2 | 12/2012 | Cappola et al. |
| 8,342,378 | B2 | 1/2013 | Marczyk et al. |
| 8,360,296 | B2 | 1/2013 | Zingman |
| 8,413,468 | B2 | 4/2013 | Pigorini |
| 8,413,868 | B2 | 4/2013 | Cappola |
| 8,414,577 | B2 * | 4/2013 | Boudreaux ........... A61B 46/10 606/41 |
| 8,424,736 | B2 | 4/2013 | Scirica et al. |
| 8,499,992 | B2 | 8/2013 | Whitman et al. |
| 8,506,557 | B2 | 8/2013 | Zemlok et al. |
| 8,517,241 | B2 | 8/2013 | Nicholas et al. |
| 8,573,460 | B2 | 11/2013 | Cappola |
| 8,573,463 | B2 | 11/2013 | Scirica et al. |
| 8,574,463 | B2 | 11/2013 | Tani et al. |
| 8,584,919 | B2 * | 11/2013 | Hueil ............... A61B 17/07207 227/176.1 |
| 8,608,043 | B2 | 12/2013 | Scirica |
| 8,608,045 | B2 | 12/2013 | Smith et al. |
| 8,622,894 | B2 | 1/2014 | Banik et al. |
| 8,672,205 | B2 | 3/2014 | Leitner |
| 8,684,247 | B2 | 4/2014 | Scirica et al. |
| 8,684,249 | B2 | 4/2014 | Racenet et al. |
| 8,685,004 | B2 | 4/2014 | Zemlock et al. |
| 8,695,865 | B2 | 4/2014 | Smith et al. |

(56) References Cited

U.S. PATENT DOCUMENTS

| | | |
|---|---|---|
| 8,708,211 B2 | 4/2014 | Zemlok et al. |
| 8,708,213 B2 | 4/2014 | Shelton et al. |
| 8,806,973 B2 | 8/2014 | Ross et al. |
| 8,820,607 B2 | 9/2014 | Marczyk |
| 8,888,762 B2 | 11/2014 | Whitman |
| 8,888,814 B2 | 11/2014 | Cappola |
| 8,894,647 B2 | 11/2014 | Beardsley et al. |
| 8,910,847 B2 | 12/2014 | Nalagatla et al. |
| 8,925,783 B2 | 1/2015 | Zemlok et al. |
| 9,113,876 B2 | 8/2015 | Racenet et al. |
| 9,155,529 B2 | 10/2015 | Beardsley et al. |
| 9,204,876 B2 | 12/2015 | Cappola et al. |
| 9,232,944 B2 | 1/2016 | Cappola et al. |
| 9,265,585 B2 | 2/2016 | Wingardner et al. |
| 9,320,519 B1 | 4/2016 | Knodel |
| 9,364,218 B2 | 6/2016 | Scirica |
| 9,364,226 B2 | 6/2016 | Zemlok et al. |
| 9,393,016 B2 | 7/2016 | Scirica et al. |
| 9,445,810 B2 | 9/2016 | Cappola |
| 9,465,873 B1 | 10/2016 | Franke et al. |
| 9,474,528 B2 | 10/2016 | Marczyk |
| 9,498,216 B2 | 11/2016 | Williams |
| 9,504,520 B2 | 11/2016 | Worrell et al. |
| 9,522,029 B2 | 12/2016 | Yates et al. |
| 9,539,006 B2 | 1/2017 | Collings et al. |
| 9,554,803 B2 * | 1/2017 | Smith .................... A61B 90/98 |
| 9,629,623 B2 | 4/2017 | Lytle et al. |
| 9,636,091 B2 | 5/2017 | Beardsley et al. |
| 9,655,617 B2 | 5/2017 | Cappola |
| 9,668,731 B2 | 6/2017 | Zemlok et al. |
| 9,668,735 B2 | 6/2017 | Beetel |
| 9,801,679 B2 | 10/2017 | Trees et al. |
| 9,820,738 B2 * | 11/2017 | Lytle, IV ............... G16H 40/63 |
| 9,839,425 B2 | 12/2017 | Zergiebel et al. |
| 9,861,358 B2 | 1/2018 | Marczyk et al. |
| 9,867,675 B2 | 1/2018 | Beardsley et al. |
| 9,872,673 B2 | 1/2018 | Beardsley et al. |
| 9,918,713 B2 | 3/2018 | Zergiebel et al. |
| 9,931,739 B2 | 4/2018 | Nelson et al. |
| 9,968,276 B2 | 5/2018 | Koktzoglou |
| 9,987,029 B2 | 6/2018 | Beardsley et al. |
| 9,993,258 B2 * | 6/2018 | Shelton, IV ..... A61B 17/32002 |
| 10,004,504 B2 | 6/2018 | Bryant |
| 10,098,637 B2 | 10/2018 | Zergiebel et al. |
| 10,105,139 B2 * | 10/2018 | Yates ........................ H02P 7/28 |
| 10,383,634 B2 | 8/2019 | Shelton et al. |
| 10,433,842 B2 * | 10/2019 | Amariglio ............ A61B 17/072 |
| 10,646,271 B2 | 5/2020 | Trees et al. |
| 10,856,871 B2 | 12/2020 | Somekh et al. |
| 11,103,247 B2 * | 8/2021 | Amariglio ........ A61B 17/07207 |
| 11,166,723 B2 | 11/2021 | Somekh et al. |
| 11,617,583 B2 | 4/2023 | Somekh et al. |
| 11,622,764 B2 | 4/2023 | Marecki et al. |
| 12,089,846 B2 | 9/2024 | Marecki et al. |
| 12,268,391 B2 | 4/2025 | Somekh et al. |
| 2001/0030219 A1 | 10/2001 | Green et al. |
| 2004/0232199 A1 | 11/2004 | Shelton et al. |
| 2005/0006429 A1 | 1/2005 | Wales et al. |
| 2005/0116009 A1 | 6/2005 | Milliman |
| 2006/0079912 A1 | 4/2006 | Whitfield et al. |
| 2006/0111210 A1 | 5/2006 | Hinman |
| 2007/0125826 A1 * | 6/2007 | Shelton ............ A61B 17/07207 |
| | | 227/176.1 |
| 2007/0257080 A1 | 11/2007 | Kamins et al. |
| 2007/0262116 A1 | 11/2007 | Hueil et al. |
| 2008/0017693 A1 | 1/2008 | Mastri et al. |
| 2008/0083810 A1 | 4/2008 | Marczyk |
| 2008/0114315 A1 | 5/2008 | Voegele et al. |
| 2008/0179374 A1 | 7/2008 | Beardsley et al. |
| 2008/0296346 A1 | 12/2008 | Shelton et al. |
| 2008/0314958 A1 | 12/2008 | Scirica |
| 2009/0062614 A1 | 3/2009 | Adzich et al. |
| 2009/0145947 A1 | 6/2009 | Scirica et al. |
| 2009/0206131 A1 | 8/2009 | Weisenburgh et al. |
| 2009/0272614 A1 | 11/2009 | Watarai |
| 2010/0001036 A1 | 1/2010 | Marczyk et al. |
| 2010/0012700 A1 | 1/2010 | Perron et al. |
| 2010/0094091 A1 | 4/2010 | Cappola |
| 2010/0264193 A1 * | 10/2010 | Huang ................. A61B 17/068 |
| | | 227/176.1 |
| 2011/0009850 A1 | 1/2011 | Main et al. |
| 2011/0062211 A1 | 3/2011 | Ross et al. |
| 2011/0166585 A1 | 7/2011 | Roth et al. |
| 2011/0253765 A1 * | 10/2011 | Nicholas .......... A61B 17/00234 |
| | | 227/175.1 |
| 2011/0290854 A1 | 12/2011 | Timm et al. |
| 2011/0295313 A1 | 12/2011 | Kerr |
| 2012/0074194 A1 | 3/2012 | Miller et al. |
| 2012/0080477 A1 | 4/2012 | Leimbach et al. |
| 2012/0116391 A1 | 5/2012 | Houser et al. |
| 2012/0286019 A1 * | 11/2012 | Hueil ................... A61B 17/068 |
| | | 227/175.1 |
| 2012/0286020 A1 | 11/2012 | Smith et al. |
| 2012/0293103 A1 | 11/2012 | Forster et al. |
| 2013/0030428 A1 | 1/2013 | Worrell et al. |
| 2013/0053831 A1 | 2/2013 | Johnson et al. |
| 2013/0092719 A1 | 4/2013 | Kostrzewski |
| 2013/0098966 A1 | 4/2013 | Kostrzewski et al. |
| 2013/0168435 A1 | 7/2013 | Huang et al. |
| 2013/0199327 A1 | 8/2013 | Park et al. |
| 2013/0245676 A1 | 9/2013 | Cappola |
| 2013/0304115 A1 * | 11/2013 | Miyamoto .............. A61B 17/28 |
| | | 606/205 |
| 2014/0001231 A1 | 1/2014 | Shelton et al. |
| 2014/0025103 A1 | 1/2014 | Hundertmark et al. |
| 2014/0148803 A1 | 5/2014 | Taylor |
| 2014/0224856 A1 | 8/2014 | Smith et al. |
| 2014/0263543 A1 | 9/2014 | Leimbach et al. |
| 2014/0276949 A1 | 9/2014 | Staunton et al. |
| 2014/0305988 A1 | 10/2014 | Boudreaux et al. |
| 2014/0305994 A1 | 10/2014 | Parihar et al. |
| 2015/0053749 A1 | 2/2015 | Shelton et al. |
| 2015/0196966 A1 | 7/2015 | Tsai |
| 2015/0196996 A1 | 7/2015 | Nelson et al. |
| 2015/0209059 A1 | 7/2015 | Trees et al. |
| 2015/0297216 A1 | 10/2015 | Williams |
| 2015/0342605 A1 | 12/2015 | Abbott et al. |
| 2015/0374396 A1 * | 12/2015 | Strobl ................ A61B 18/1445 |
| | | 606/207 |
| 2016/0058441 A1 | 3/2016 | Morgan et al. |
| 2016/0074106 A1 | 3/2016 | Garrison |
| 2016/0089175 A1 | 3/2016 | Hibner et al. |
| 2016/0166250 A1 | 6/2016 | Marczyk |
| 2016/0249945 A1 | 9/2016 | Shelton et al. |
| 2016/0270786 A1 | 9/2016 | Scirica |
| 2017/0000485 A1 | 1/2017 | Shelton et al. |
| 2017/0172577 A1 | 6/2017 | Wenchell et al. |
| 2017/0224334 A1 | 8/2017 | Worthington et al. |
| 2017/0224343 A1 | 8/2017 | Baxter et al. |
| 2017/0252096 A1 | 9/2017 | Felder et al. |
| 2017/0281177 A1 | 10/2017 | Harris et al. |
| 2017/0281184 A1 * | 10/2017 | Shelton, IV ....... A61B 17/1155 |
| 2017/0281220 A1 | 10/2017 | Hibner et al. |
| 2018/0021041 A1 | 1/2018 | Zhang et al. |
| 2018/0021082 A1 | 1/2018 | Trees et al. |
| 2018/0042637 A1 | 2/2018 | Craig et al. |
| 2018/0078354 A1 | 3/2018 | Cardinale et al. |
| 2018/0091145 A1 | 3/2018 | Dey et al. |
| 2018/0153545 A1 | 6/2018 | Zergiebel et al. |
| 2018/0168575 A1 | 6/2018 | Simms et al. |
| 2018/0168599 A1 | 6/2018 | Bakos et al. |
| 2018/0289370 A1 | 10/2018 | Amariglio et al. |
| 2018/0310935 A1 | 11/2018 | Wixey |
| 2018/0317915 A1 | 11/2018 | Mcdonald |
| 2018/0368832 A1 | 12/2018 | Marecki et al. |
| 2019/0000439 A1 | 1/2019 | Gustafson |
| 2019/0133593 A1 | 5/2019 | P V R |
| 2019/0183491 A1 | 6/2019 | Shelton et al. |
| 2019/0261984 A1 | 8/2019 | Nelson et al. |
| 2019/0290265 A1 | 9/2019 | Shelton et al. |
| 2020/0008801 A1 | 1/2020 | Somekh et al. |
| 2020/0015818 A1 | 1/2020 | Amariglio et al. |
| 2020/0046362 A1 | 2/2020 | Baril et al. |
| 2020/0093486 A1 | 3/2020 | Somekh et al. |

(56) References Cited

U.S. PATENT DOCUMENTS

| | | |
|---|---|---|
| 2020/0222046 A1 | 7/2020 | Somekh et al. |
| 2020/0405293 A1 | 12/2020 | Shelton et al. |
| 2021/0007740 A1 | 1/2021 | Marecki et al. |
| 2021/0085323 A1 | 3/2021 | Somekh et al. |
| 2022/0133318 A1 | 5/2022 | Hudson et al. |
| 2022/0183688 A1 | 6/2022 | Moy et al. |
| 2022/0218335 A1 | 7/2022 | Baxter, III et al. |
| 2022/0296232 A1 | 9/2022 | Adams et al. |
| 2022/0338874 A1 | 10/2022 | Marecki et al. |
| 2022/0387025 A1 | 12/2022 | Marecki et al. |
| 2023/0092719 A1 | 3/2023 | Marbach et al. |
| 2023/0165584 A1 | 6/2023 | Leimbach et al. |
| 2023/0233207 A1 | 7/2023 | Somekh et al. |
| 2023/0233208 A1 | 7/2023 | Marecki et al. |
| 2023/0371954 A1 | 11/2023 | Bear et al. |
| 2024/0050093 A1 | 2/2024 | Marecki et al. |
| 2025/0009352 A1 | 1/2025 | Marecki et al. |
| 2025/0114094 A1 | 4/2025 | Marecki et al. |

FOREIGN PATENT DOCUMENTS

| | | |
|---|---|---|
| CN | 1985768 B | 9/2011 |
| CN | 101194853 B | 7/2012 |
| CN | 101965156 B | 12/2012 |
| CN | 108542464 A | 9/2018 |
| DE | 112019002420 T5 | 3/2021 |
| EP | 1563791 A1 | 8/2005 |
| EP | 1563792 A1 | 8/2005 |
| EP | 1563794 A1 | 8/2005 |
| EP | 1709911 A1 | 10/2006 |
| EP | 1021130 B1 | 11/2006 |
| EP | 1908410 A1 | 4/2008 |
| EP | 2253277 A1 | 11/2010 |
| EP | 2253278 A1 | 11/2010 |
| EP | 2586382 A3 | 9/2013 |
| EP | 2777530 A1 | 9/2014 |
| EP | 2839786 A1 | 2/2015 |
| EP | 2886020 A1 | 6/2015 |
| EP | 2886071 A1 | 6/2015 |
| EP | 2484290 B1 | 7/2015 |
| EP | 2942022 A1 | 11/2015 |
| EP | 2311385 B1 | 5/2017 |
| WO | 2004075728 A2 | 9/2004 |
| WO | 2016107586 A1 | 7/2016 |
| WO | 2018035796 A1 | 3/2018 |

OTHER PUBLICATIONS

Final Office Action received in U.S. Appl. No. 15/481,949 dated May 29, 2019, 15 pages.

International Search Report and Written Opinion dated Apr. 7, 2020 for PCT Application No. PCT/US2020/013694 filed Jan. 15, 2020, 8 pages.

International Search Report and Written Opinion dated Jun. 18, 2018 for PCT Application No. PCT/US2018/025988 filed Apr. 4, 2018, 8 pages.

International Search Report and Written Opinion dated May 25, 2023 for PCT Application No. PCT/US2023/014366 Filed Mar. 2, 2013, 8 pages.

International Search Report and Written Opinion dated Oct. 22, 2018 for PCT Application No. PCT/ US2018/038909 filed Jun. 22, 2018, 10 pages.

International Search Report and Written Opinion dated Oct. 4, 2019 for PCT Application No. PCT/US2019/040315 filed Jul. 2, 2018, 9 pages.

International Search Report and Written Opinion received in PCT App No. PCT/US24/52666 dated Dec. 20, 2024.

International Search Report and Written Opinion received in PCT/US2022/032434 dated Oct. 19, 2022, 11 pages.

Non Final Office Action received in U.S. Appl. No. 15/481,949 dated Mar. 18, 2019, 22 pages.

Non Final Office Action received in U.S. Appl. No. 16/249,520 dated Jul. 27, 2020, 10 pages.

Non Final Office Action received in U.S. Appl. No. 17/113,865 dated Sep. 19, 2022, 13 pages.

Non Final Office Action received in U.S. Appl. No. 17/241,538 dated Aug. 16, 2022, 10 pages.

Non Final Office Action received in U.S. Appl. No. 17/686,730 dated Jan. 8, 2024, 10 pages.

Non Final Office Action received in U.S. Appl. No. 18/129,317 dated Dec. 8, 2023, 8 pages.

Non Final Office Action received in U.S. Appl. No. 18/129,324 dated Jan. 19, 2024, 9 pages.

Non-Final Office Action received in U.S. Appl. No. 18/496,107 dated Dec. 12, 2024, 55 pages.

Non-Final Office Action received in U.S. Appl. No. 17/833,302 dated Jan. 30, 2025, 51 pages.

Notice of Allowance received in U.S. Appl. No. 16/249,520 dated Nov. 3, 2020, 8 pages.

Notice of Allowance received in U.S. Appl. No. 16/577,097 dated Sep. 13, 2021, 8 pages.

Notice of Allowance received in U.S. Appl. No. 16/582,829 dated May 14, 2021, 7 pages.

Notice of Allowance received in U.S. Appl. No. 17/133,865 dated Dec. 7, 2022; 9 pages.

Notice of Allowance received in U.S. Appl. No. 17/241,538 dated Jan. 11, 2023, 9 pages.

Notice of Allowance received in U.S. Appl. No. 17/686,730 dated Apr. 16, 2024, 7 pages.

Notice of Allowance received in U.S. Appl. No. 17/686,730 dated Aug. 5, 2024, 8 pages.

Notice of Allowance received in U.S. Appl. No. 18/125,314 dated Nov. 8, 2024, 19 pages.

Notice of Allowance received in U.S. Appl. No. 18/129,317 dated Jul. 17, 2024, 7 pages.

Notice of Allowance received in U.S. Appl. No. 18/129,317 dated Mar. 21, 2024, 7 pages.

Notice of Allowance received in U.S. Appl. No. 18/129,324 dated May 15, 2024, 7 pages.

Notice of Allowance received in U.S. Appl. No. 15/481,949 dated Aug. 14, 2019, 10 pages.

Restriction Requirement received in U.S. Appl. No. 18/496,107 dated Sep. 24, 2024, 14 pages.

Final Office Action received in U.S. Appl. No. 18/496,107 dated Apr. 7, 2025, 35 pages.

Notice of Allowance dated Apr. 9, 2025 for U.S. Appl. No. 17/833,302, 13 pages.

Notice of Allowance received in U.S. Appl. No. 18/129,317 dated Feb. 18, 2025, 13 pages.

* cited by examiner

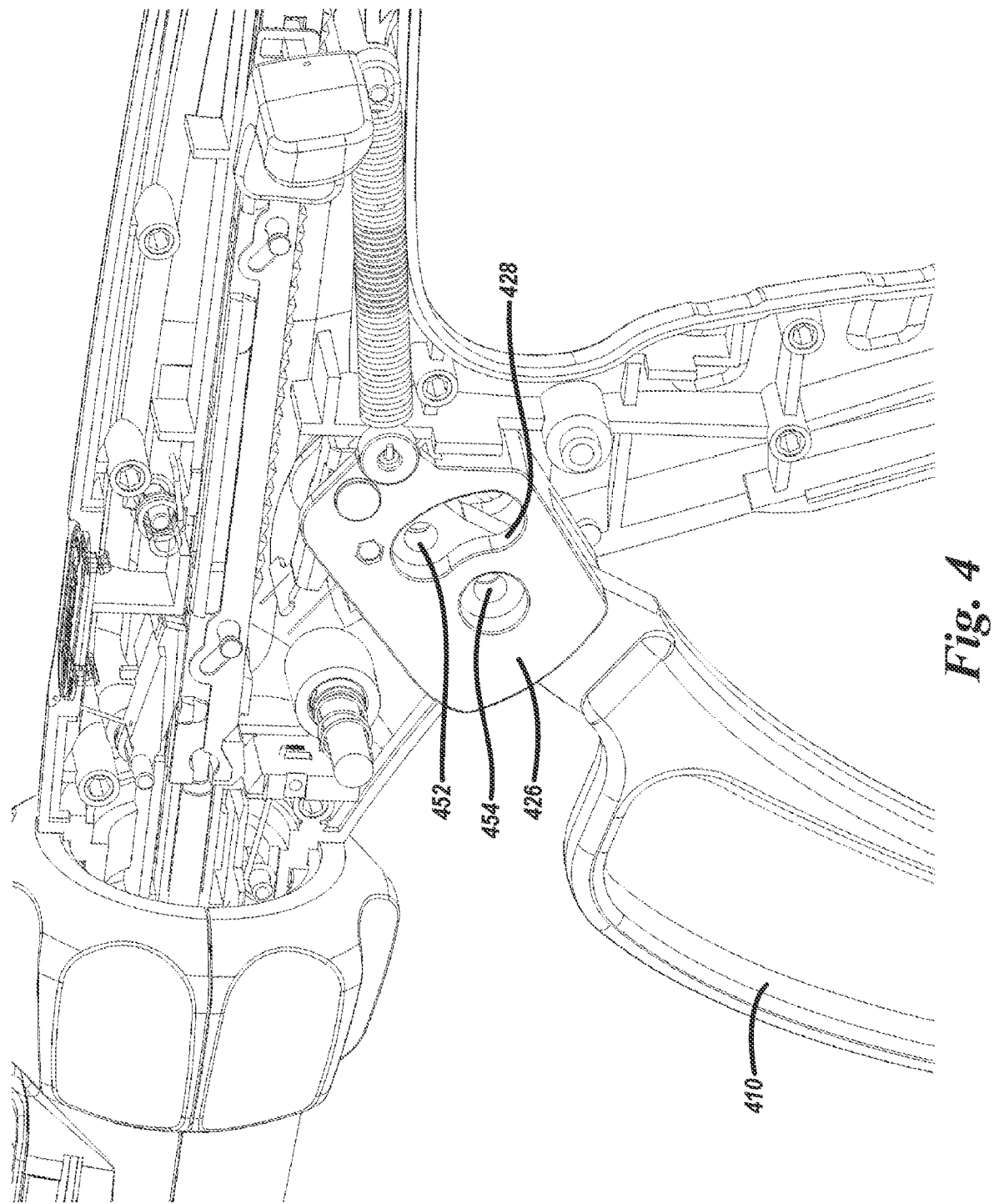

SURGICAL HANDLE ASSEMBLY

PRIORITY INFORMATION

This application claims benefit of U.S. Non-Provisional application Ser. No. 16/582,829 filed Sep. 25, 2019, and issued as U.S. Pat. No. 11,103,247 on Aug. 31, 2021, which claims the benefit of U.S. Non-Provisional application Ser. No. 15/481,949 filed Apr. 7, 2017 and issued as U.S. Pat. No. 10,433,842 on Oct. 8, 2019, the specifications of which are incorporated herein by reference.

TECHNICAL FIELD

The present disclosure relates generally to a surgical handle assembly, and more particularly, to a surgical handle assembly configured to provide two or more modes of operation.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

BRIEF DESCRIPTION OF THE DRAWINGS

FIG. 4 is a schematic diagram of a surgical handle assembly including a first opening, a second opening, and a slot in accordance with a number of embodiments of the present disclosure.

DETAILED DESCRIPTION

Figure 1:
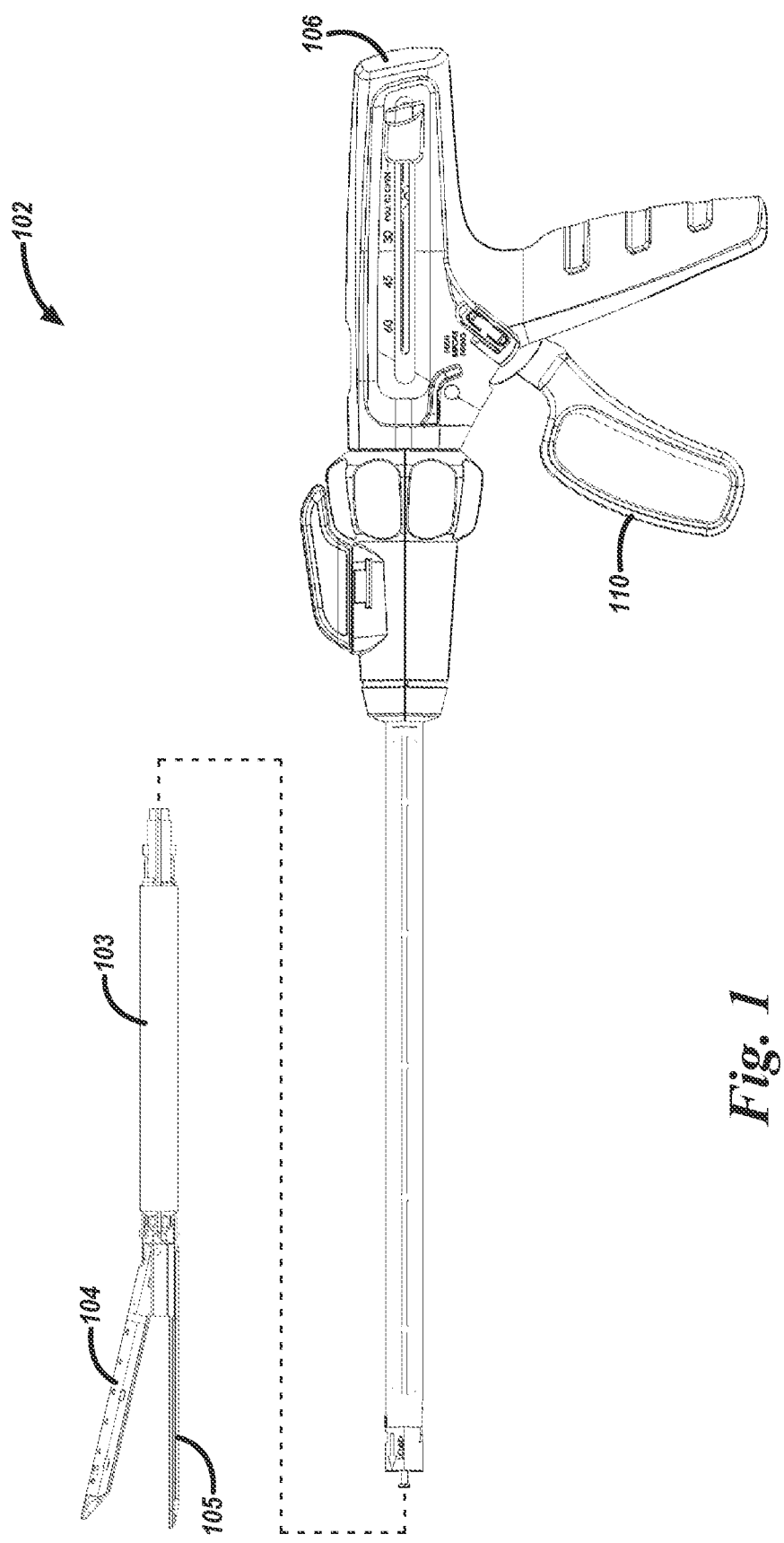
FIG. 1 is a schematic diagram of a surgical stapling apparatus including a surgical handle assembly in accordance with a number of embodiments of the present disclosure.

The present disclosure includes apparatuses for a surgical handle assembly. An example apparatus includes a movable handle member and mode selection capability, e.g. a switch, configured to provide two or more modes of operation for the movable handle member. A driving pawl can be pivotally connected to a swing wheel to advance an actuation shaft linearly in a distal direction in response to actuation of the movable handle member.

In a number of embodiments, the mode selection capability can be a switch. The surgical handle assembly is described with the switch example throughout the present disclosure for ease of understanding and illustration; however embodiments are not limited to a switch. For example, the switch can include a first pin and a second pin to set modes of operation. While a first pin and a second pin are shown by example, more than two pins and/or two modes of operation are included in the embodiments disclosed herein. In this example, the first pin when set to a particular position can provide a first mode of operation for the movable handle member. The second pin when set to a particular position can provide a second mode of operation for the movable handle member. Use of the surgical handle assembly with a surgical stapler in the first mode of operation can advance an actuation shaft a first distance in the distal direction and coupled to a reloadable cartridge can deploy a first number of staples. Use of the surgical handle assembly with a surgical stapler in the second mode of operation can advance an actuation shaft a second distance in a distal direction and coupled to a reloadable cartridge can deploy a second, different number of staples. In a number of embodiments, the first mode of operation or the second mode of operation can be selected based on the type of tissue being fastened, a number of staples to be deployed, speed of staples being deployed, and/or an amount of force to be applied by a user to actuate the movable handle member, for example. A mode of operation can be selected based on the type of tissue being fastened, for example, when the tissue is thick, the user may use a mode that requires less force to be applied. A mode that requires less force also may be used when the user is fatigued or physically unable to use a mode that requires more force, for example. A mode of operation can be selected based on speed of staples being deployed to lower edema, e.g. less blood in area being stapled, to allow stapling of tissue rather than blood.

In a number of embodiments, the movable handle member may be coupled to a swing wheel. In this manner, the movable handle member and swing wheel may pivot around the first pin at a first pivot point during a first mode. The first pin can be connected to the movable handle member via a first opening in the swing wheel and movable handle member to engage the movable handle member. In a number of embodiments, the movable handle member and swing wheel may pivot around the second pin at a second pivot point during a second mode. The second pin can be connected to the movable handle member via a second opening in the swing wheel and movable handle member to engage the movable handle member. The second pin is not coupled to the movable handle member via the second opening while in the first mode of operation. The first pin is not coupled to the movable handle member via the first opening while in the second mode of operation.

In a number of embodiments, transition from the first mode of operation to the second mode of operation can be accomplished by removing the first pin from the first opening while engaging the second pin with the second opening.

The switch may be moved from a first position to a second position in order to engage and/or disengage the first and second pins with their respective openings. Transition from the second mode of operation to the first mode of operation can be accomplished by removing the second pin from the second opening while engaging the first pin with the first opening. Here, the switch may be moved from a second position to a first position to engage and/or disengage the first and second pins with their respective openings.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

As used herein, designators such as "X", "Y", "N", "M", etc., particularly with respect to reference numerals in the drawings, indicate that a number of the particular feature so designated can be included. It is also to be understood that the terminology used herein is for the purpose of describing particular embodiments only, and is not intended to be limiting. As used herein, the singular forms "a", "an", and "the" can include both singular and plural referents, unless the context clearly dictates otherwise. In addition, "a number of", "at least one", and "one or more" (e.g., a number of pivot points) can refer to one or more pivot points, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled" and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 210 may reference element "10" in FIG. 2A, and a similar element may be referenced as 310 in FIG. 3A. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of a surgical stapling apparatus 102 including a surgical handle assembly 106 in accordance with a number of embodiments of the present disclosure. In the example, a surgical stapler apparatus 102 can include a surgical handle assembly 106 and a reloadable cartridge assembly 103. As shown in the example of FIG. 1, the reloadable cartridge assembly 103, e.g. a disposable loading unit, can be releasably secured to a distal end of an elongated body of the surgical handle assembly 106. In this example, the reloadable cartridge assembly 103 can include a first elongated member 104 and a second elongated member 105 that can be used to clamp tissue. One of the elongated members can house one or more staple cartridges. The other elongated member can have an anvil that can be used to form a staple when driven from the staple cartridge. As mentioned, a surgical stapling apparatus 102 can receive reloadable cartridge assemblies having rows of staples. In a number of embodiments, third party reloadable cartridge and/or reloadable cartridge assemblies may be used with the surgical handle assembly 106 and embodiments of surgical handle assembly 106 may be configured to receive the same. A staple can be ejected by actuation of a movable handle member 110 that is a part of a surgical handle assembly 106 to the surgical stapling apparatus 102. Actuation of the movable handle member 110 can actuate the actuation shaft (e.g. actuation shaft 240 in FIG. 2A) to eject a number of staples. For example, in a first mode of operation, actuation of the movable handle member 110 may eject 30 staples. In a second mode, actuation of the movable handle member 110 may eject 60 staples. However, embodiments are not limited to a particular number of staples ejected in the first or second mode. Further, embodiments are not limited to use with a surgical stapling apparatus. The surgical handle assembly 106 is described with the surgical stapling apparatus 102 example throughout the present disclosure for ease of understanding and illustration.

Figure 2A:
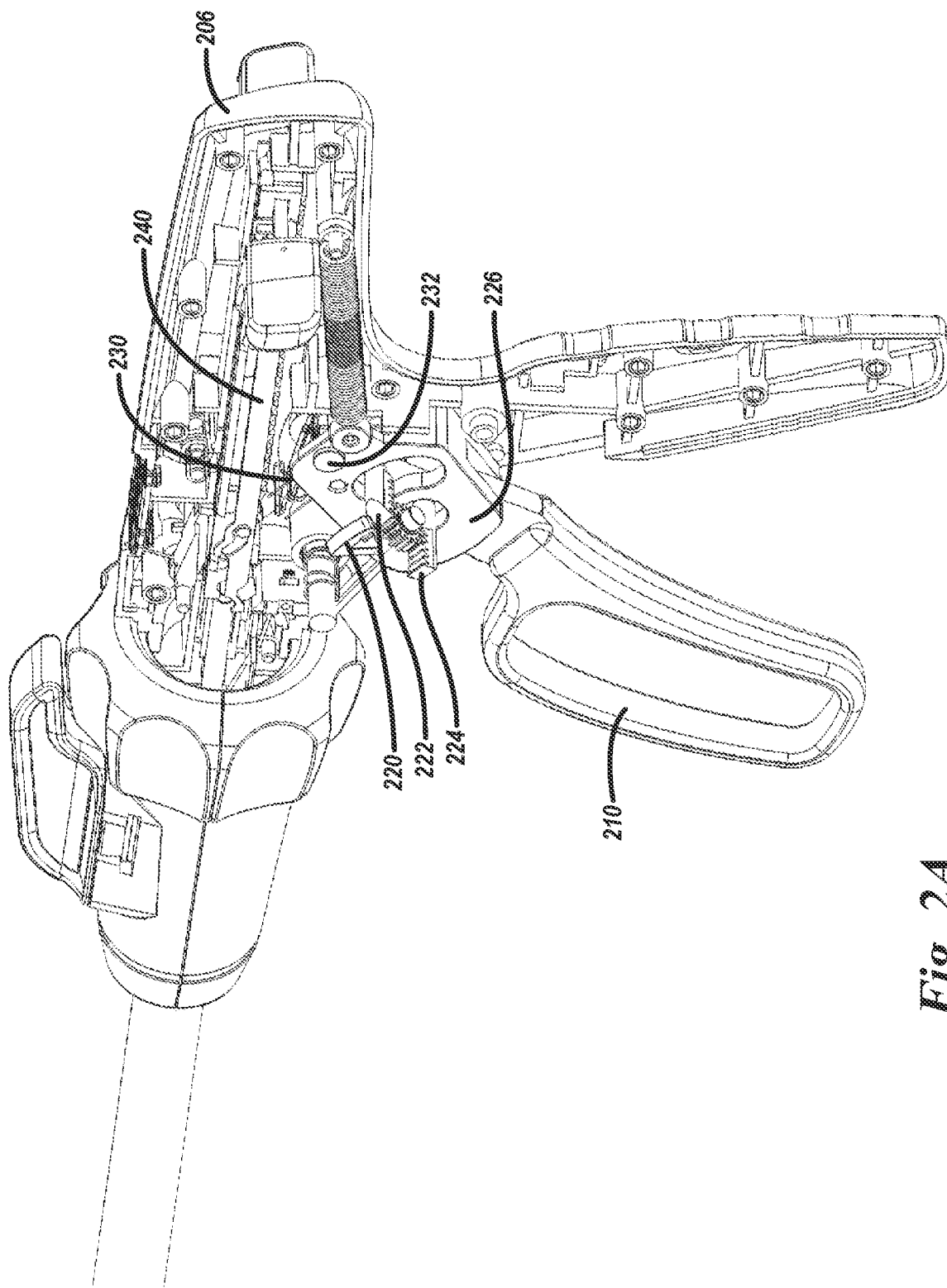
FIG. 2A is a schematic diagram of a surgical handle assembly in a first mode and a first movable handle member position in accordance with a number of embodiments of the present disclosure.

FIG. 2A is a schematic diagram of a surgical handle assembly in a first mode and in a first movable handle member position (e.g., "ready" position) in accordance with a number of embodiments of the present disclosure. The surgical handle apparatus 206 can include a movable handle member 210, a switch 220, and a driving pawl 230. The switch 220 can provide two or more modes of operation for the movable handle member 210. The driving pawl 230 in a number of embodiments can be pivotally connected to a swing wheel 226 and can be configured to advance an actuation shaft 240 linearly in a distal direction in response to actuation of the movable handle member 210.

In a number of embodiments, the surgical handle assembly 206 can be in a first mode, as shown in FIG. 2A. The surgical handle assembly 206, in a first mode, can have a first distance (e.g. distance 513 in FIG. 5) between a pivot point around first pin 222 to a coupling pin 232 of the driving pawl 230. The surgical handle assembly 206, in a second mode, can have a second distance (e.g. distance 515 in FIG. 5) between a pivot point around second pin 224 to the coupling pin 232 of the driving pawl 230. In this example, the second distance (e.g. distance 515 in FIG. 5) is longer than the first distance (e.g. first distance 513 in FIG. 5). In a number of embodiments, a number of pivot points can exist and a pivot point can be around a pin placed in an opening in the movable handle 210. In FIG. 2A, in the first mode, a first pin 222 can be coupled to the movable handle member 210 in a first opening and a second pin 224 can be disengaged from the second opening (e.g. second opening 454 in FIG. 4) so as not to be coupled to the movable handle member 210. In the first mode the first pin 222 can serve as the pivot point for the movable handle member 210 with the first distance (e.g. distance 513 in FIG. 5) between the pivot point and coupling pin 232. In a second mode, a second pin 224 can be coupled to the movable handle member 210. In this example, the first pin 222 can be disengaged from the first opening (e.g. first opening 452 in FIG. 4) so as not to be coupled to the movable handle member 210. In the second mode the second pin 224 can serve as the pivot point for the movable handle member 210. In this example, the second distance (e.g. distance 515 in FIG. 5) is longer than the first distance (e.g. first distance 513 in FIG. 5). As such, in the first mode, when the first pin 222 is the pivot point, an amount of force used to advance the actuation shaft 240 linearly in a distal direction is less than an amount of force used to advance the actuation shaft 240 linearly in the distal direction in a second mode of operation, using the second pin 224 as the pivot point. In this example, the amount of force used is less in the first mode than in the second mode due to the distance between the pivot point and the coupling pin 232 of the driving pawl 230 and because the travel distance is less.

In a number of embodiments, the surgical handle assembly 206 can be in a first mode. In a first mode, the surgical handle assembly 206 can operate to advance the actuation shaft 240 a third distance (e.g. distance 544 in FIG. 5). The third distance (e.g. distance 544 in FIG. 5) is a length of advance of the actuation shaft 240 in a distal direction, upon actuation of the movable handle member 210 in the first mode. The surgical handle assembly 206 can alternatively be changed to a second mode of operation. In a second mode, the surgical handle assembly 206 can operate to advance the actuation shaft 240 a fourth distance (e.g. distance 546 in FIG. 5). The fourth distance (e.g. distance 546 in FIG. 5) is a length of advance of the actuation shaft 240 in the distal direction upon actuation of the movable handle member 210 in the second mode. In this example, the fourth distance (e.g. distance 546 in FIG. 5) is longer than the third distance (e.g. third distance 544 in FIG. 5).

In a number of embodiments, the surgical handle assembly 206 can be in a ready position, as shown in FIG. 2A. In the ready position, the surgical handle assembly 206 is ready to advance the actuation shaft 240 linearly in a distal direction upon actuation of the movable handle member 210.

Figure 2B:
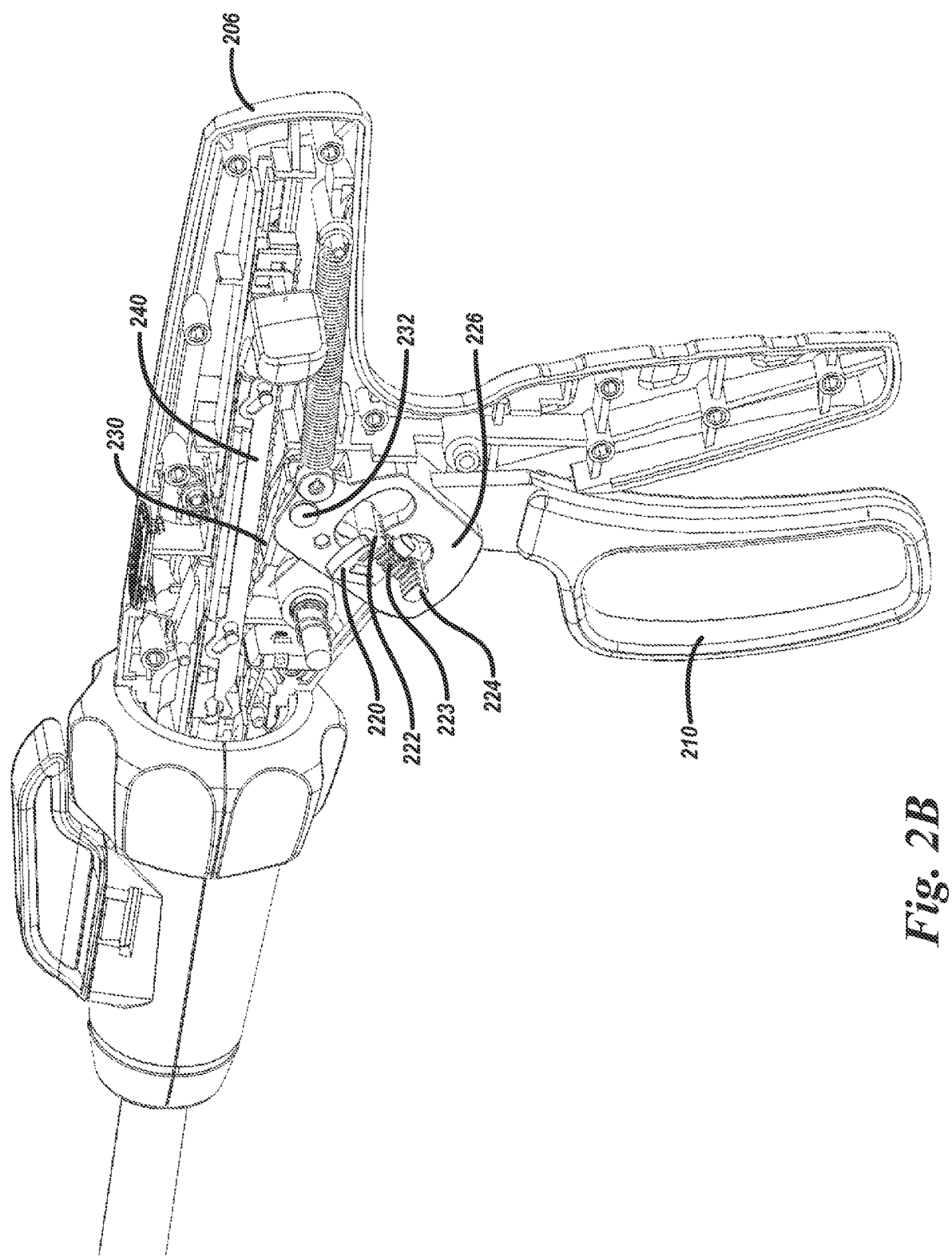
FIG. 2B is a schematic diagram of a surgical handle assembly in a first mode and a second movable handle member position in accordance with a number of embodiments of the present disclosure.

FIG. 2B is a schematic diagram of a surgical handle assembly in a first mode and a second movable handle member position (e.g. a "compressed" and/or "closed" position) in accordance with a number of embodiments of the present disclosure. The surgical handle assembly 206 can include a movable handle member 210, a switch 220, and a driving pawl 230. The switch 220 can provide two or more modes of operation for the movable handle member 210. The driving pawl 230 in a number of embodiments can be pivotally connected to a swing wheel 226 and can be configured to advance an actuation shaft 240 linearly in a distal direction in response to actuation of the movable handle member 210.

In a number of embodiments, the surgical handle assembly 206 can be in a first mode, as shown in FIG. 2B. The surgical handle assembly 206, in a first mode, can have a first distance (e.g. distance 513 in FIG. 5) between the pivot point around first pin 222 to a coupling pin 232 of the driving pawl 230. The surgical handle assembly 206, in a second mode, can have a second distance (e.g. distance 515 in FIG. 5) from the pivot point around second pin 224 to the coupling pin 232 of the driving pawl 230. In this example, the second distance (e.g. distance 515 in FIG. 5) is longer than the first distance (e.g. distance 513 in FIG. 5). In a number of embodiments, a number of pivot points can exist and a pivot point can be around a pin placed in an opening in the movable handle 210. In FIG. 2B, in the first mode, the first pin 222 can be coupled to the movable handle member 210 in a first opening (e.g. first opening 452 in FIG. 4) and the second pin 224 can be disengaged from a second opening (e.g. second opening 454 in FIG. 4) so as not to be coupled to the movable handle member 2010. In the first mode, the first pin 222 can serve as the pivot point for the movable handle member 210 with the first distance (e.g. distance 513 in FIG. 5) between the pivot point and coupling pin 232. In the second mode the second pin 224 can serve as the pivot point for the movable handle member 210. In this example, the second distance (e.g. distance 515 in FIG. 5) is longer than the first distance (e.g. distance 513 in FIG. 5). Again, in the first mode, when the first pin 222 is the pivot point, an amount of force used to advance the actuation shaft 240 linearly in a distal direction is less than an amount of force used to advance the actuation shaft linearly in the distal direction in a second mode of operation, using the second pin 224 as the pivot point. In this example, the amount of force is less in the first mode than in the second mode due to the distance between the pivot point and the coupling pin 232 of the driving pawl 230 and the travel distance is less.

Figure 5:
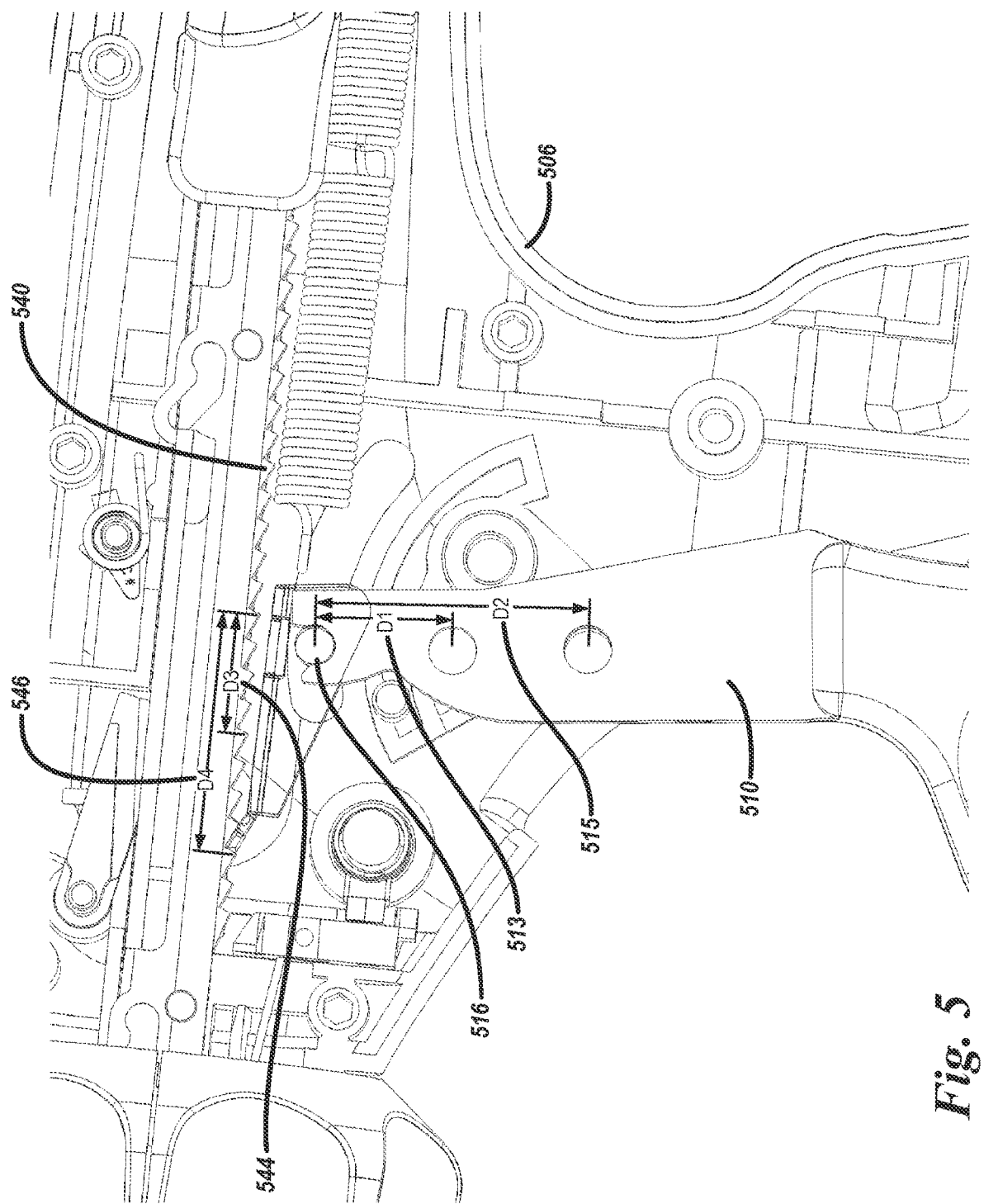
FIG. 5 is a schematic diagram of a surgical handle assembly including a coupling point opening in accordance with a number of embodiments of the present disclosure.

In a first mode, the surgical handle assembly 206 can operate to advance the actuation shaft 240 a third distance (e.g. third distance 544 in FIG. 5). The third distance (e.g. distance 544 in FIG. 5) is a length of advance of the actuation shaft 240 in a distal direction, upon actuation of the movable handle member 210. The surgical handle assembly 206 can be in a second mode. In a second mode, the surgical handle assembly 206 can operate to advance the actuation shaft 240 a fourth distance (e.g. distance 546 in FIG. 5). The fourth distance (e.g. distance 546 in FIG. 5) is a length of advance of the actuation shaft 240 in the distal direction. In this example, the fourth distance (e.g. distance 546 in FIG. 5) is longer than the third distance (e.g. distance 544 in FIG. 5). In a number of embodiments the fourth distance can be twice as long as the third distance. As such, the actuation shaft 240 can be advanced twice as far in the second mode than in the first mode In a number of embodiments, the surgical handle assembly 206 can be in a closed position, as shown in FIG. 2B. As will be explained more in connection with FIG. 4. In a closed position, the surgical handle assembly 206 can prevent the actuation shaft 240 from moving linearly in a distal and/or proximal direction upon release of the movable handle member 210 by having the driving pawl 230 disengage from teeth of a ratchet associated with the actuation shaft 240 and reengage with teeth further back at a starting point of the ratchet.

In a number of embodiments, the pivot point of the surgical handle assembly 206 can be changed using the switch 220. In an example, the switch 220, when actuated, can rotate a gear 223. The gear 223 can contact one or more gears of the first pin 222 and one or more gears of the second pin 224. The surgical handle assembly 206 can be placed in the first mode when the switch 220 is actuated in a first direction. When the switch 220 is actuated in the first direction, the gear 223 can rotate in a first rotational direction. When the gear 223 is rotated in a first rotational direction the gear 223 can insert the first pin 222 into a first opening (e.g. first opening 452 in FIG. 4) and can remove the second pin 224 from a second opening (e.g. second opening 454 in FIG. 4). The surgical handle assembly 206 can be placed in the second mode when the switch 220 is actuated in a second direction. When the switch 220 is actuated in the second direction the gear can rotate in a second rotational direction. When the gear 223 is rotated in a second rotational direction the gear 223 can insert the second pin 224 into a second opening (e.g. second opening 454 in FIG. 4) and can remove the first pin 222 from the first opening (e.g. first opening 452 in FIG. 4). This example is used throughout the present disclosure for ease of understanding and illustration. Embodiments are not limited to a gear (e.g., gear 223 in FIG. 2A, for example) to transition between modes of operation. A number of mechanisms (e.g. a switch) to insert and remove a number of pins in a number of openings in a moveable handle member for operation in a number of modes can be used in accordance with a number of embodiments of the present disclosure to transition between modes of operation. For example, a push pin can be used to switch the surgical handle assembly 206 from one mode to another. A switch can be coupled to a first pin and a second pin such that when the first pin is pushed into the first opening (e.g. first opening 452 in FIG. 4) the second pin is removed from the second opening (e.g. second opening 454 in FIG. 4). As well as when the second pin is pushed into the second opening (e.g. second opening 454 in FIG. 4) the first pin is removed from the first opening (e.g. first opening 452 in FIG. 4).

Figure 3A:
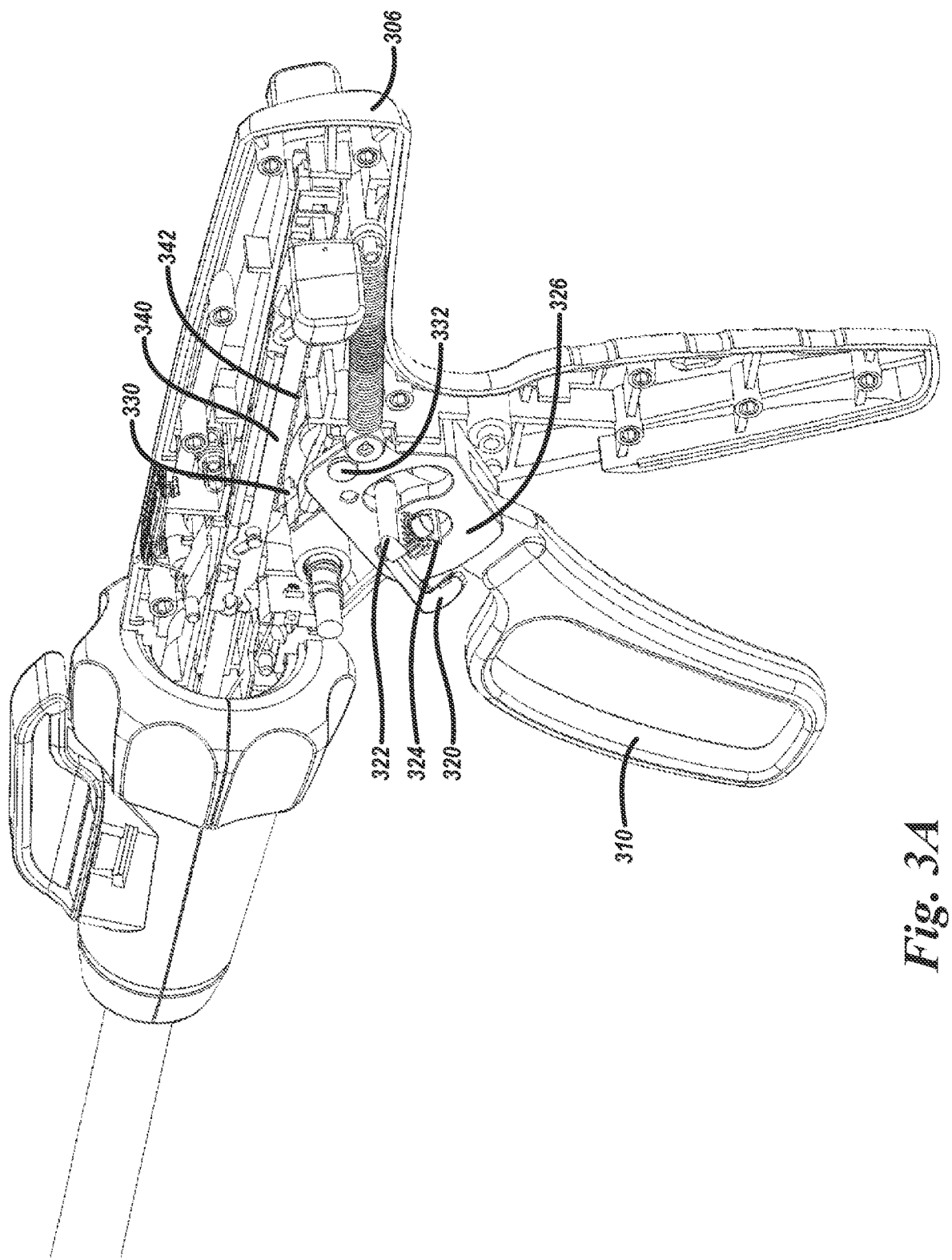
FIG. 3A is a schematic diagram of a surgical handle assembly in a second mode and a first movable handle member position in accordance with a number of embodiments of the present disclosure.

FIG. 3A is a schematic diagram of a surgical handle assembly in a second mode and a first movable handle position (e.g., "ready" position) in accordance with a number of embodiments of the present disclosure. The surgical handle assembly 306 can include a movable handle member 310, a switch 320, and a driving pawl 330. The switch 320 can provide two or more modes of operation for the movable handle member 310. The driving pawl 330 in a number of embodiments can be pivotally connected to the swing wheel 326 and can be configured to advance an actuation shaft 340 linearly in a distal direction in response to actuation of the movable handle member 310.

In a number of embodiments, the surgical handle assembly 306 can be in a second mode, as shown in FIG. 3A. The surgical handle assembly 306, in a second mode, can have a second distance (e.g. distance 515 in FIG. 5) between the pivot point around a second pin 324 to the coupling pin 332 of the driving pawl 330. In this example, the second distance is longer than the first distance (e.g. distance 513 in FIG. 5). In a number of embodiments a number of pivot points can exist and a pivot point can be around a pin placed in an opening in the movable handle 310. In FIG. 3A, in a second mode, a second pin 324 can be coupled to the movable handle member 310. In this example, the first pin 322 can be disengaged from the first opening (e.g. first opening 452 in FIG. 4) so as not to be coupled to the movable handle member 310. In the second mode the second pin 324 can serve as the pivot point for the movable handle member 310. In a number of embodiments, the driving pawl 330 is configured to contact a toothed rack 342 of the actuation shaft 340 to advance the actuation shaft linearly in a distal direction. The actuation shaft 340 can be advanced in response to actuation of the movable handle member 310. In this example, the second distance (e.g. distance 515 in FIG. 5) is longer than the first distance (e.g. first distance 513 in FIG. 5). As such, when the second pin 324 is the pivot point, the second mode operation advances twice as many ratchets of the toothed rack 342 than the first mode of operation. In this example, twice as many ratchets are advanced in the second mode due to the distance between the pivot point and the coupling pin 332 of the driving pawl 330.

In a number of embodiments, a swing wheel 326 is connected to the movable handle member 310. Also, in a number of embodiments, the movable handle member can include a coupling opening (e.g. coupling opening 516 in FIG. 5). The swing wheel 326 and the coupling opening (e.g. coupling opening 516 in FIG. 5) can be used in the second mode of operation to allow transfer of force from the movable handle member 310 to the driving pawl 330. Transferring the force from the movable handle member 310 to the driving pawl 330 allows the actuation shaft 340 to advance linearly in the distal direction.

In a number of embodiments, the surgical handle assembly 306 can be in a ready position, as shown in FIG. 3A. In the ready position the surgical handle assembly 306 is ready to advance the actuation shaft 340 linearly in a distal direction upon actuation of the movable handle member 310.

Figure 3B:
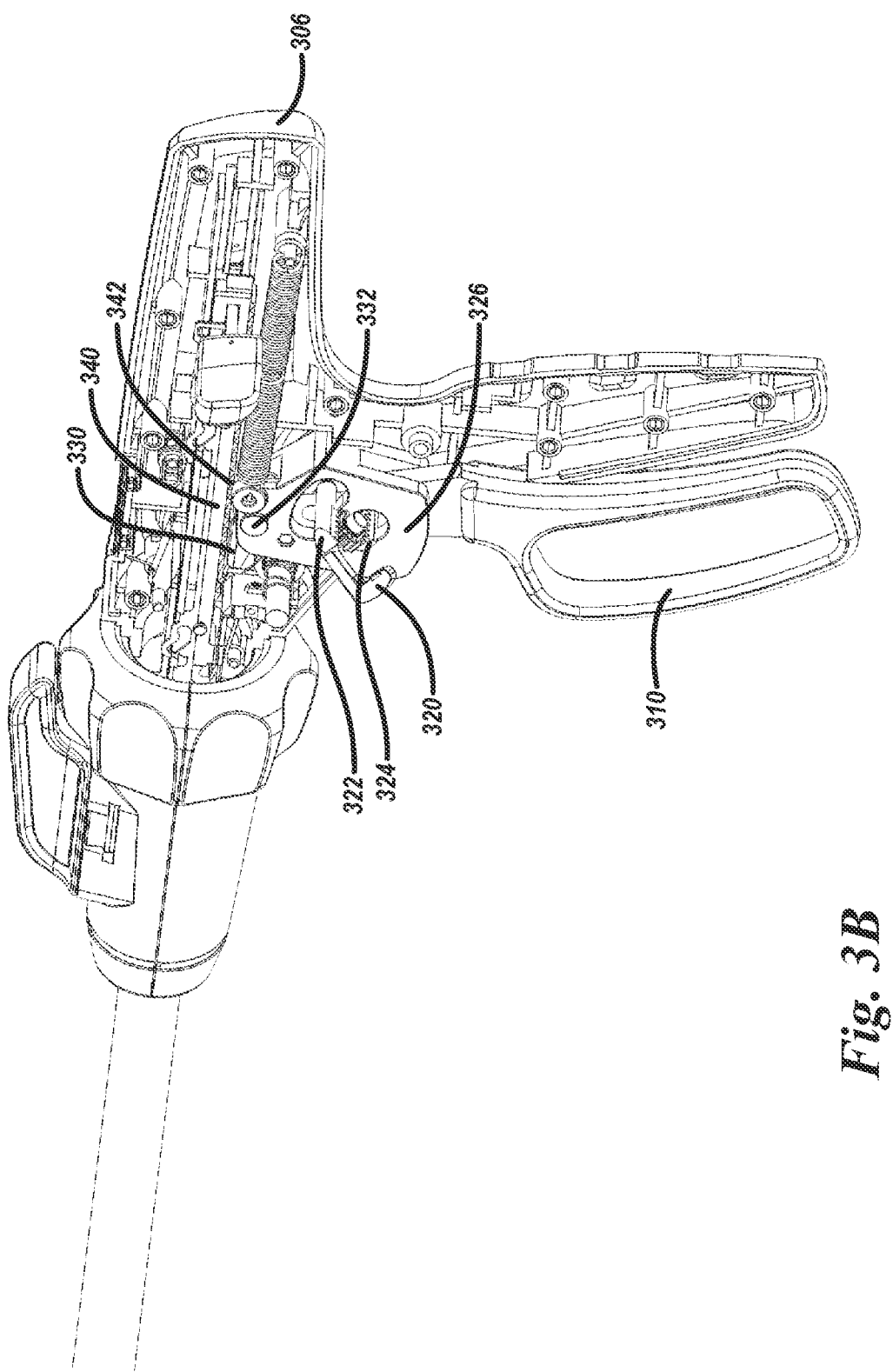
FIG. 3B is a schematic diagram of a surgical handle assembly in a second mode and a second movable handle member position in accordance with a number of embodiments of the present disclosure.

FIG. 3B is a schematic diagram of a surgical handle assembly in a second mode and a second movable handle member position (e.g. a "compressed" and/or "closed" position) in accordance with a number of embodiments of the present disclosure. The surgical handle assembly 306 can include a movable handle member 310, a switch 320, and a driving pawl 330. The switch 320 can provide two or more modes of operation for the movable handle member 310. The driving pawl 330 in a number of embodiments can be pivotally connected to the swing wheel 326 and can be configured to advance an actuation shaft 340 linearly in a distal direction in response to actuation of the movable handle member 310.

In a number of embodiments, the surgical handle assembly 306 can be in a second mode, as shown in FIG. 3B. The surgical handle assembly 306, in the second mode, can have a second distance (e.g. second distance 515 in FIG. 5) from the pivot point around the second pin 324 to the coupling pin 332 of the driving pawl 330. In this example, the second distance (e.g. distance 515 in FIG. 5) is longer than the first distance (e.g. first distance 513 in FIG. 5). In a number of embodiments a number of pivot points can exist and a pivot point can be around a pin placed in an opening in the movable handle 310. In a second mode, a second pin 324 can be coupled to the movable handle member 310. In this example, the first pin 322 can be disengaged from the first opening (e.g. first opening 452 in FIG. 4) so as not to be coupled to the movable handle member 310. In the second mode the second pin 324 can serve as the pivot point for the movable handle member 310. In the second mode the second pin 324 can serve as the pivot point for the movable handle member 310. In this example, the second distance (e.g. distance 515 in FIG. 5) is longer than the first distance (e.g. distance 513 in FIG. 5). In a number of embodiments, the driving pawl 330 is configured to contact a toothed rack 342 of an actuation shaft 340 to advance the actuation shaft linearly in a distal direction in response to actuation of the movable handle member 310. In this example, the second distance (e.g. distance 515 in FIG. 5) is longer than the first distance (e.g. first distance 513 in FIG. 5). As such, when the second pin 324 serves as the pivot point, the second mode of operation advances the actuation shaft 340 twice as far and advances twice as many ratchets of the toothed rack than the first mode of operation. In this example, the actuation shaft 340 is advanced twice as far and twice as many ratchets are advanced in the second mode due to the distance between the pivot point and the coupling pin 332 of the driving pawl 330.

In a number of embodiments, the surgical handle assembly 306 can be in a closed position, as shown in FIG. 3B. In a closed position, the surgical handle assembly 306 can prevent the actuation shaft 340 from moving linearly in a distal and/or proximal direction upon release of the movable handle member 310.

FIG. 4 is a schematic diagram of a surgical handle assembly including a first opening, a second opening, and a slot in accordance with a number of embodiments of the present disclosure. In FIG. 4, the movable handle member 410 can include a first opening 452 and a second opening 454. The first pin (e.g. first pin 222 in FIG. 2A) can be inserted into the first opening 452 for the first mode. The second pin (e.g. second pin 224 in FIG. 2A) can be inserted into the second opening 454 for the second mode. In a number of embodiments, the swing wheel 426 can include a slot 428. The slot 428 can allow the swing wheel 426 to rotate whether the first pin (e.g. first pin 222 in FIG. 2A) is inserted into the first opening 452 or the first pin (e.g. first pin 222 in FIG. 2A) is removed from the first opening 452.

FIG. 5 is a schematic diagram of a surgical handle assembly including a coupling opening 516 in accordance with a number of embodiments of the present disclosure. In a number of embodiments, the movable handle member 510 can include a coupling opening 516. The coupling pin (e.g. coupling pin 232 in FIG. 2A) can be pivotally connected to the coupling opening 516. The coupling opening 516 can allow the actuation shaft 540 to advance linearly in the distal direction without coupling pin 232 binding due to the shape of the coupling opening 516. The coupling opening 516 shape, for example, can be a "U" shape, e.g. saddle, allowing degrees of translation and movement in contrast to being a fixed point.

In a number of embodiments, the surgical handle assembly 506 can be in a first mode. In the first mode, the first pin (e.g. first pin 222 in FIG. 2A) serves as the pivot point, having a first distance 513. In a second mode, the second pin (e.g. second pin 224 in FIG. 2A) serves as the pivot point, having a second distance 515. In this example, the second distance 515 is longer than the first distance 513.

In a number of embodiments, the surgical handle assembly 506 can be in a first mode having a third distance 544. The third distance 544 is a length of advance of the actuation shaft 540 in the distal direction. The surgical handle assembly 506 can be in a second mode having a fourth distance 546. The fourth distance 546 is a length of advance of the actuation shaft 540 in the distal direction. In this example, the fourth distance 546 is longer than the third distance 544.

FIG. 5 illustrates the surgical handle assembly 506 in a second mode and the movable handle member 510 in a closed position. The driving pawl (e.g. driving pawl 230 in FIG. 2A), in this example, is at the end of the fourth distance 546 and has fully advanced the actuation shaft 540 for an actuation of the movable handle member 510 in the second mode of operation. In a first mode and when the movable handle member 510 is in a closed position, the driving pawl (e.g. driving pawl 230 in FIG. 2A) can be at the end of the third distance 544 and has fully advanced the actuation shaft 540 for an actuation of the movable handle member 510 in the first mode of operation.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical handle assembly apparatus, comprising:
   a movable handle member;
   an actuation shaft; and
   a switch configured to: (a) provide a first mode of operation for the movable handle member by connecting a first pin to the movable handle member via a first opening and (b) provide a second mode of operation for the movable handle member by connecting a second pin to the movable handle member via a second opening,
   wherein, in the first mode of operation, the actuation shaft is advanced linearly in a distal direction a first distance in response to actuation of the movable handle member,
   wherein, in the second mode of operation, the actuation shaft is advanced linearly in the distal direction a second distance in response to actuation of the movable handle member, and
   wherein the first distance is different from the second distance.

2. The apparatus of claim 1, wherein:
   in the first mode of operation, a first amount of force is required to move the movable handle;
   in the second mode of operation, a second amount of force is required to move the movable handle; and
   the first amount of force is different from the second amount of force.

3. The apparatus of claim 1, further comprising a driving pawl configured to advance the actuation shaft.

4. The apparatus of claim 3, further comprising a swing wheel, wherein the driving pawl is pivotally connected to the swing wheel, and wherein the swing wheel is connected to the movable handle.

5. The apparatus of claim 1, wherein the switch includes the first pin and the second pin.

6. A surgical handle assembly apparatus, comprising:
   a movable handle member;
   a switch configured to: (a) provide a first mode of operation for the movable handle member by connecting a first pin to the movable handle member via a first opening and (b) provide a second mode of operation for the movable handle member by connecting a second pin to the movable handle member via a second opening,
   wherein, in the first mode of operation, the movable handle pivots on a first pivot point, and
   wherein, in the second mode of operation, the movable handle pivots on a second pivot point.

7. The apparatus of claim 6, further comprising an actuation shaft, wherein the actuation shaft is advanced linearly in a distal direction a first distance in response to actuation of the movable handle member during the first mode of operation, and wherein the actuation shaft is advanced linearly in the distal direction a second distance in response to actuation of the movable handle member during the second mode of operation.

8. The apparatus of claim 6, wherein;
   in the first mode of operation, a first amount of force is required to move the movable handle;
   in the second mode of operation, a second amount of force is required to move the movable handle; and the first amount of force is different from the second amount of force.

9. The apparatus of claim 6, wherein the switch includes the first pin and the second pin.

10. The apparatus of claim 6, further comprising a swing wheel connected to the movable handle.

11. The apparatus of claim 6, wherein the movable handle member pivots around the first pin at the first pivot point during the first mode of operation, and wherein the movable handle member pivots around the second pin at the second pivot point during the second mode of operation.

12. The apparatus of claim 6, further comprising a driving pawl, wherein:
   in the first and second modes of operation, the driving pawl is configured to: advance an actuation shaft linearly in a distal direction to deploy one or more staples, and
   the apparatus is configured to deploys a different number of staples in the first mode of operation than in the second mode of operation.

13. A surgical handle assembly apparatus, comprising:
   a movable handle member; and
   a switch configured to (a) provide a first mode of operation for the movable handle member by connecting a first pin to the movable handle member via a first opening and (b) to provide a second mode of operation for the movable handle member by connecting a second pin to the movable handle member via a second opening,
   wherein, in the first mode of operation, a first amount of force is required to move the movable handle,
   wherein, in the second mode of operation, a second amount of force is required to move the movable handle, and
   wherein the first amount of force is different from the second amount of force.

14. The apparatus of claim 13, further comprising a staple cartridge, wherein:
   a driving pawl is configured to: advance a toothed rack linearly in a distal direction in response to actuation of the movable handle to deploy one or more staples in the first and second modes of operation, and
   the apparatus is configured to deploys a different number of staples in the first mode of operation than in the second mode of operation.

15. The apparatus of claim 14, wherein the one or more staples are contained in a staple cartridge removably connected to the toothed rack.

16. The apparatus of claim 13, wherein a driving pawl is configured to: (i) advance a toothed rack linearly in a distal direction a first distance in response to actuation of the movable handle member during the first mode of operation and (ii) advance the toothed rack linearly in the distal direction a second distance in response to actuation of the movable handle member during the second mode of operation.

17. The apparatus of claim 13, further comprising a swing wheel connected to the movable handle member and to a driving pawl.

18. The apparatus of claim 13, wherein the first pin is not coupled to the movable handle member via the first opening during the second mode of operation.

19. The apparatus of claim 13, wherein the second pin is not coupled to the movable handle member via the second opening during the first mode of operation.

20. The apparatus of claim 13 wherein the switch includes the first pin and the second pin.

* * * * *

UNITED STATES PATENT AND TRADEMARK OFFICE
CERTIFICATE OF CORRECTION

PATENT NO. : 12,414,766 B2
APPLICATION NO. : 17/382705
DATED : September 16, 2025
INVENTOR(S) : Leon Amariglio et al.

Page 1 of 1

It is certified that error appears in the above-identified patent and that said Letters Patent is hereby corrected as shown below:

In the Claims

In Column 10, Line 11, in Claim 1, delete "to:" and insert -- to --.

In Column 10, Line 44, in Claim 6, delete "to:" and insert -- to --.

In Column 10, Line 63, in Claim 8, delete "wherein;" and insert -- wherein: --.

In Column 11, Line 15, in Claim 12, delete "to:" and insert -- to --.

In Column 11, Line 18, in Claim 12, delete "deploys" and insert -- deploy --.

In Column 12, Line 5, in Claim 14, delete "to:" and insert -- to --.

In Column 12, Line 9, in Claim 14, delete "deploys" and insert -- deploy --.

In Column 12, Line 16, in Claim 16, delete "to:" and insert -- to --.

Signed and Sealed this
Twenty-seventh Day of January, 2026

John A. Squires
*Director of the United States Patent and Trademark Office*